(12) United States Patent
Rioux et al.

(10) Patent No.: US 11,071,577 B2
(45) Date of Patent: *Jul. 27, 2021

(54) CO-ACCESS BIPOLAR ABLATION PROBE

(71) Applicant: Boston Scientific Scimed, Inc., Maple Grove, MN (US)

(72) Inventors: Robert F. Rioux, Ashland, MA (US); Paul DiCarlo, Middleboro, MA (US); Steve M. Anderson, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 435 days.

This patent is subject to a terminal disclaimer.

(21) Appl. No.: 16/003,856

(22) Filed: Jun. 8, 2018

(65) Prior Publication Data

US 2018/0303534 A1 Oct. 25, 2018

Related U.S. Application Data

(63) Continuation of application No. 13/797,817, filed on Mar. 12, 2013, now Pat. No. 9,993,278, which is a continuation of application No. 10/828,032, filed on Apr. 20, 2004, now Pat. No. 8,414,580.

(51) Int. Cl.
*A61B 18/14* (2006.01)
*A61B 18/00* (2006.01)
*A61B 10/02* (2006.01)

(52) U.S. Cl.
CPC .......... *A61B 18/00* (2013.01); *A61B 18/1477* (2013.01); *A61B 10/0275* (2013.01); *A61B 2018/00005* (2013.01); *A61B 2018/00047* (2013.01); *A61B 2018/143* (2013.01)

(58) Field of Classification Search
CPC ................ A61B 18/1477; A61B 18/00; A61B 2018/00005; A61B 2018/00047; A61B 2018/143; A61B 10/0275
See application file for complete search history.

(56) References Cited

U.S. PATENT DOCUMENTS

| | | | |
|---|---|---|---|
| 5,336,222 A | 8/1994 | Durgin, Jr. et al. | |
| 5,403,311 A | 4/1995 | Abele et al. | |
| 5,536,267 A * | 7/1996 | Edwards | ............ A61B 18/1477 604/22 |

(Continued)

OTHER PUBLICATIONS

"File History," for U.S. Appl. No. 10/828,032.

(Continued)

*Primary Examiner* — Michael F Peffley
(74) *Attorney, Agent, or Firm* — Pauly, DeVries Smith & Deffner LLC

(57) ABSTRACT

A method of treating abnormal tissue within a patient includes positioning a delivery cannula within the patient, the delivery cannula having a first electrode disposed on its distal end; introducing an ablation probe through the cannula and out an open distal end thereof, so that a second ablation electrode carried on the ablation probe contacts abnormal tissue within the patient; conveying ablation energy between the first and second ablation electrodes to ablate the abnormal tissue; and introducing a separate medical element, whether a device or a therapeutic agent, through the cannula before or after the ablation process.

20 Claims, 7 Drawing Sheets

(56) References Cited

U.S. PATENT DOCUMENTS

| | | | |
|---|---|---|---|
| 5,672,173 A * | 9/1997 | Gough | A61B 18/1815 606/41 |
| 5,674,184 A | 10/1997 | Hassler, Jr. et al. | |
| 5,807,395 A | 9/1998 | Mulier et al. | |
| 5,868,740 A | 2/1999 | Leveen et al. | |
| 5,984,919 A | 11/1999 | Hilal et al. | |
| 5,989,196 A | 11/1999 | Chu et al. | |
| 6,106,524 A | 8/2000 | Eggers et al. | |
| 6,221,039 B1 * | 4/2001 | Durgin | A61B 18/1492 604/22 |
| 6,238,393 B1 | 5/2001 | Mulier et al. | |
| 6,261,241 B1 | 7/2001 | Quick et al. | |
| 6,379,353 B1 | 4/2002 | Nichols et al. | |
| 6,478,793 B1 | 11/2002 | Rittman et al. | |
| 6,506,189 B1 | 1/2003 | Cosman et al. | |
| 6,652,520 B2 | 11/2003 | Bush et al. | |
| 6,706,039 B2 | 3/2004 | Mulier et al. | |
| 7,238,184 B2 | 7/2007 | Megerman et al. | |
| 8,414,580 B2 | 4/2013 | Rioux et al. | |
| 9,993,278 B2 | 6/2018 | Rioux et al. | |
| 2003/0040743 A1 | 2/2003 | Cosman et al. | |
| 2003/0093007 A1 * | 5/2003 | Wood | A61B 10/06 600/564 |
| 2004/0006336 A1 | 1/2004 | Swanson et al. | |
| 2004/0006339 A1 | 1/2004 | Underwood et al. | |
| 2004/0034339 A1 | 2/2004 | Stoller et al. | |
| 2004/0082938 A1 | 4/2004 | Ohyama et al. | |
| 2004/0215184 A1 | 10/2004 | Eggers et al. | |
| 2005/0059964 A1 | 3/2005 | Fitz et al. | |
| 2005/0090762 A1 | 4/2005 | Burbank et al. | |
| 2005/0203505 A1 | 9/2005 | Megerman et al. | |
| 2005/0234443 A1 | 10/2005 | Rioux et al. | |
| 2013/0190756 A1 | 7/2013 | Rioux et al. | |

OTHER PUBLICATIONS

"File History," for U.S. Appl. No. 13/797,817.
"International Preliminary Report on Patentability," for PCT Application No. PCT/US2005/009085 dated Oct. 25, 2006 (5 pages).
"International Search Report and Written Opinion," for PCT Application No. PCT/US2005/009085 dated Jul. 13, 2005 (6 pages).

* cited by examiner

CO-ACCESS BIPOLAR ABLATION PROBE

RELATED APPLICATION DATA

This application is a continuation of U.S. patent application Ser. No. 13/797,817, filed Mar. 12, 2013, now granted as U.S. Pat. No. 9,993,278, which is a continuation of U.S. patent application Ser. No. 10/828,032, filed Apr. 20, 2004, now granted as U.S. Pat. No. 8,414,580, the contents of each of which are incorporated herein by reference in their entirety as though set forth in full.

FIELD OF THE INVENTION

The field of the invention relates generally to the structure and use of radio frequency (RF) ablation probes for the treatment of tissue.

BACKGROUND OF THE INVENTION

The delivery of radio frequency (RF) energy to target regions within solid tissue is known for a variety of purposes of particular interest to the present invention. In one particular application, RF energy may be delivered to diseased regions (e.g., tumors) for the purpose of ablating predictable volumes of tissue with minimal patient trauma.

In a typical procedure, tissue suspected of containing an abnormality is imaged using a high definition imaging modality, such as Magnetic Resonance Imaging (MRI). If an abnormality, such as a tumor, is discovered, a sample of the abnormal tissue is retrieved. This is typically accomplished by percutaneously introducing a biopsy needle through healthy tissue into contact with the abnormal tissue. Proper guidance and placement of the biopsy needle is facilitated by the use of a standard imaging modality, such as fluoroscopy. The biopsy needle, with the tissue sample, is then removed from the patient's body, and the tissue sample is placed into a container and sent to a laboratory to examine whether it is malignant or benign. In the interim, the physician and/or patient may decide to treat the tumor, whether or not the tumor is actually malignant or benign. In this case, the abnormal tissue would typically be treated immediately after performing the biopsy. Alternatively, the physician and/or patient may decide to treat the tumor only if it is indeed malignant, in which case, such malignancy would be treated after receiving the laboratory results.

In either case, the tumor can be treated by percutaneously introducing an RF ablation probe through the patient's body into contact with the tumor in a similar manner that the biopsy needle was described above. The ablation probe can then be operated to ablate the tumor. The interstitial space left by the removal of the tumor can then be treated with a therapeutic agent, such as a drug. Typically, this is accomplished by introducing a separate drug delivery device into the patient's body in the same manner as the biopsy needle and ablation probe was, and delivering the drug into the interstitial space.

RF ablation of tumors is currently performed using one of two core technologies. The first technology uses a single needle electrode, which when attached to a RF generator, emits RF energy from the exposed, uninsulated portion of the electrode. This energy translates into ion agitation, which is converted into heat and induces cellular death via coagulation necrosis. The second technology utilizes multiple needle electrodes, which have been designed for the treatment and necrosis of tumors in the liver and other solid tissues. U.S. Pat. No. 6,379,353 discloses such a probe, which comprises a delivery cannula and an electrode deployment member reciprocatably mounted within the delivery cannula to alternately deploy an electrode array from the delivery cannula and retract electrode array within the delivery cannula. The individual electrodes within the array have spring memory, so that they assume a radially outward, arcuate configuration as they are deployed from the delivery cannula. In general, a multiple electrode array creates a larger lesion than that created by a single needle electrode.

When creating lesions using ablation electrode element (whether a single needle electrode or needle electrode array, deployable or otherwise) RF energy is commonly delivered to the tissue in one of several ways. In one arrangement, RF current may be delivered to an ablation electrode element in a monopolar fashion, which means that current will pass from the ablation electrode element to a dispersive electrode attached externally to the patient, e.g., using a contact pad placed on the patient's flank. In another arrangement, the RF current is delivered to two electrodes in a bipolar fashion, which means that current will pass between "positive" and "negative" electrodes in close proximity to each other, e.g., two electrodes on the same probe or array. Bipolar arrangements, which require the RF energy to traverse through a relatively small amount of tissue between the tightly spaced electrodes, are more efficient than monopolar arrangements, which require the RF energy to traverse through the thickness of the patient's body. As a result, bipolar electrode arrays generally create larger and/or more efficient lesions than monopolar electrode arrays. Additionally, bipolar arrangements are generally safer for the physician and patient, since there is an ever-present danger that the physician and patient may become a ground in the monopolar arrangement, resulting in painful burns.

Although the current treatment of tumors is generally successful, there is still room for improvement. For example, even though such treatments can be considered minimally invasive in that open surgery is not required, they still require multiple instrument insertions during the biopsy, ablation, and drug delivery steps—causing tissue trauma with each insertion. Notably, even if the biopsy needle, ablation probe, and drug delivery device are introduced through the same opening in the skin, they will tend to take different tissue paths to the tumor. In addition, the patient must be imaged each time an instrument is guided through the patient's body into contact with the tumor. As such, the patient may have to be imaged several times during biopsy, ablative treatment, and drug delivery. Also, even though tumors come in all shapes and sizes, lesions resulting from a particular bipolar arrangement will typically have the same geometry, since the electrodes that make up a typical bipolar arrangement are fixed relative to each other. As such, some tumors may not be efficiently ablated using a standard bipolar ablation probe.

Thus, there is a need for a tumor treatment kit and method that minimizes the number of instruments that must be inserted into the patient's body and provides for a more efficient bipolar ablation of the tumor.

SUMMARY OF THE INVENTION

In accordance with a first aspect of the present invention, a medical probe kit is provided. The kit comprises a cannula having a shaft, a lumen extending through the cannula shaft, and a first ablation electrode disposed on the distal end of the cannula shaft. The cannula may have a handle mounted to the proximal end of the cannula shaft, and an optional fluid delivery port on the handle in fluid communication with the cannula lumen.

The kit further comprises an ablation probe configured to be removably disposed within the delivery cannula lumen. The ablation probe has a shaft and a second ablation electrode disposed on a distal end of the probe shaft, wherein the first and second ablation electrodes are arranged in a bipolar configuration. Preferably, the ablation probe is slidable relative to the delivery cannula, whereby the distance between the first and second ablation electrodes can be adjusted. The ablation electrodes can be variously formed on the cannula shaft and probe shaft. For example, the shafts can be electrically conductive, and at least portions of the shafts can have an insulative coating, leaving the remaining portions of the shafts to form the electrodes.

In the preferred embodiment, the probe shaft is rigid, but may also be flexible if desired. In the preferred embodiment, the probe shaft has a tissue-penetrating tip, so as to facilitate introduction of the cannula through tissue. Depending on the manner in which the cannula is to be introduced through tissue, the probe shaft may have a closed tip or an open tip. In the former case, the closed tip minimizes tissue trauma if desired. In the latter case, the ablation probe can be used to core tissue, e.g., in order to retrieve a tissue sample. The probe shaft may alternatively have a blunted tip, e.g., if the cannula can be introduced through tissue by itself, or with the aid of another device, such as an obturator or trocar. The kit optionally includes a biopsy stylet configured to be removably disposed within the cannula lumen.

In one alternative embodiment, the kit comprises a plurality of ablation probe configured to be removably disposed in the cannula lumen. Alternatively, the cannula may have a plurality of lumens extending through the cannula lumen, in which case, the ablation probes can be configured to be removably disposed in the respective cannula lumens. Each of the ablation probes comprises a shaft and an ablation electrode disposed on the distal end of the shaft, wherein the first ablation electrode is arranged in a bipolar configuration with the plurality of ablation electrodes.

In accordance with a second aspect of the present invention, a method of treating abnormal tissue within a patient is provided. The method comprises introducing a delivery cannula within the patient, e.g., percutaneously through the patient's skin, and introducing an ablation probe through a lumen within the cannula into contact with the abnormal tissue. In the preferred method, the ablation probe can be used to penetrate the tissue. Alternatively, the ablation probe can be used to core the tissue, e.g., in order to retrieve a tissue sample.

The method further comprises conveying ablation energy between the first and second electrodes located on the respective cannula and ablation probe to ablate the abnormal tissue. In the preferred method, the distance between the first and second electrodes is adjusted by sliding the ablation probe relative to the delivery cannula. In this case, the ablation energy is conveyed between the first and second electrodes while the first and second electrodes are maintained from each other at the adjusted distance. Optionally, the abnormal tissue is cooled during the tissue ablation to provide for a more efficient ablation process.

The method further comprises introducing a medical element through the cannula lumen into contact with the abnormal tissue. The medical element can be, e.g., a biopsy stylet, a chemotherapeutic agent, or an obturator, such as a trocar. Thus, it can be appreciated that both the ablation probe and medical element can be interchangeably used in the cannula. For example, the medical element can be removed prior to introducing the ablation probe through the cannula lumen, or the ablation probe can be removed from the cannula lumen prior to introducing the ablation probe through the cannula lumen.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
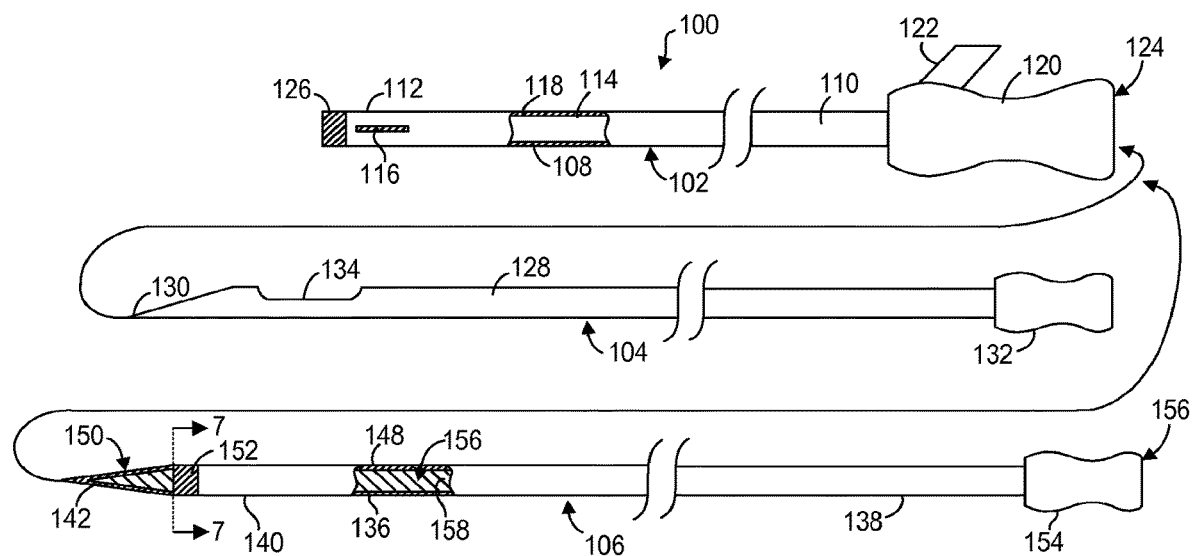
FIG. 1 is a plan view of a tissue treatment kit arranged in accordance with one preferred embodiment of the present inventions, wherein a delivery cannula, biopsy stylet, and ablation probe are particularly shown.

FIG. 1 illustrates a tissue treatment kit 100 arranged in accordance with a preferred embodiment of the present invention. The tissue treatment kit 100 generally comprises a delivery cannula 102 that can be percutaneously introduced within a patient, a biopsy stylet 104 configured for removing a tissue sample from the patient, and an ablation probe 106 configured for therapeutically ablating tissue. The biopsy stylet 104 and ablation probe 106 are configured to be alternately introduced through the delivery cannula 102 in contact with the tissue to be treated.

The delivery cannula 102 comprises a cannula shaft 108 having a proximal end 110 and a distal end 112, and a delivery lumen 114 extending through the cannula shaft 108. As will be described in further detail below, the cannula shaft 108 may be rigid, semi-rigid, or flexible, depending upon the designed means for introducing the delivery cannula 102 to the target tissue. The distal end 112 of the cannula shaft 108 preferably carries a visualization marker 116 to allow the physician to identify the orientation of the cannula 102. The visualization marker 116 may be an ultrasound, MRI or other visualization marker known to those of skill in the art.

In the preferred embodiment, the cannula shaft 108 is composed of an electrically conductive material, such as stainless steel. In this case, the exterior surface of the cannula shaft 108, with the exception of the tip of the distal end 112, is preferably composed of an electrically insulative material 118. Alternatively, the cannula shaft 108 may be composed of an electrically insulative material, such as a medical grade plastic, in which case, a separate insulative coating is not needed. The cannula shaft 108 has a suitable length, typically in the range from 5 cm to 30 cm, preferably from 10 cm to 20 cm, an outside diameter consistent with its intended use, typically being from 1 mm to 5 mm, usually from 1.3 mm to 4 mm, and an inner diameter typically being from 0.7 mm to 4 mm, preferably from 1 mm to 3.5 mm.

The cannula 102 further comprises a handle 120 mounted to the proximal end 110 of the cannula shaft 108. The handle 120 is preferably composed of a durable and rigid material, such as medical grade plastic, and is ergonomically molded to allow a physician to more easily manipulate the cannula 102. The handle 120 comprises an electrical connector 122 with which an RF cable (not shown) mates. The handle 120 also comprises a fluid delivery port 124, which is in communication with the delivery lumen 114. As will be described in further detail below, the biopsy stylet 104, ablation probe 106, and chemotherapeutic agents can be interchangeably introduced into the delivery lumen 114 via the delivery port 124.

The cannula 102 further comprises an RF ablation electrode 126 carried by the distal end 112 of the cannula shaft 108. In the preferred embodiment, the electrode 126 is formed by the exposed distal tip portion of the cannula shaft 108, in which case, the electrical connector 122 is electrically coupled to the electrode 126 via the electrically conductive cannula shaft 108. Alternatively, if the cannula shaft 108 is composed of an electrically insulative material, the distal cannula tip can be coated with an electrically conductive material to form the electrode thereon, or a discrete ring electrode can be interference fit on the distal cannula case. In this alternative case, a separate RF wire (not shown) will need to be routed from the electrode back through the cannula shaft 108 to the electrical connector 122, preferably through the wall of the cannula shaft 108 so as to not hinder the delivery of the ablation probe 106 and biopsy stylet 104 through the delivery lumen 114.

Figure 3:
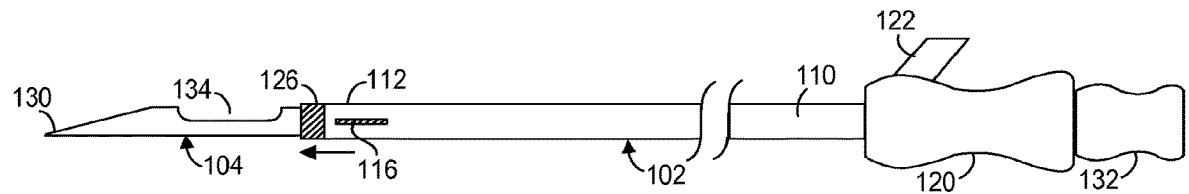
FIG. 3 is a side view of the combination of the delivery cannula and stylet used in the kit of FIG. 1.

The biopsy stylet 104 comprises a solid elongated shaft 128 with a tissue-penetrating distal tip 130 and a proximal handle 132. The biopsy stylet 104 may operated in a standard manner to obtain a tissue sample. For example, in the illustrated embodiment, the biopsy stylet 104 comprises a grooved notch 134 just proximal to the distal tip 130. Referring to FIG. 3, when the stylet 104 is advanced from the cannula 102 to expose the notch 134, the tissue prolapses into the notch 134, and then the cannula 102 can be advanced, thereby shearing the tissue to sever the sample. The sample is held protected inside the notch 134. The stylet 104 can then be removed from the delivery lumen 114 in order to retrieve the tissue sample. Further details regarding the structure and use of biopsy stylets in association with cannulae are disclosed in U.S. Pat. No. 5,989,196, which is expressly incorporated herein by reference.

The ablation probe 106 comprises an elongated shaft 136 having a proximal end 138 and a distal end 140. The probe shaft 136 is preferably composed of a rigid or semi-rigid material, such that the probe shaft 136 can be introduced through solid tissue to the target tissue site when deployed from the cannula 102. The distal end 140 of the probe shaft 136 comprises a closed tissue-penetrating tip 142, which allows the cannula 102, in combination with the ablation probe 106 (combination shown in FIG. 4), to be more easily introduced through tissue, while preventing tissue coring and minimizing tissue trauma.

Figure 2:
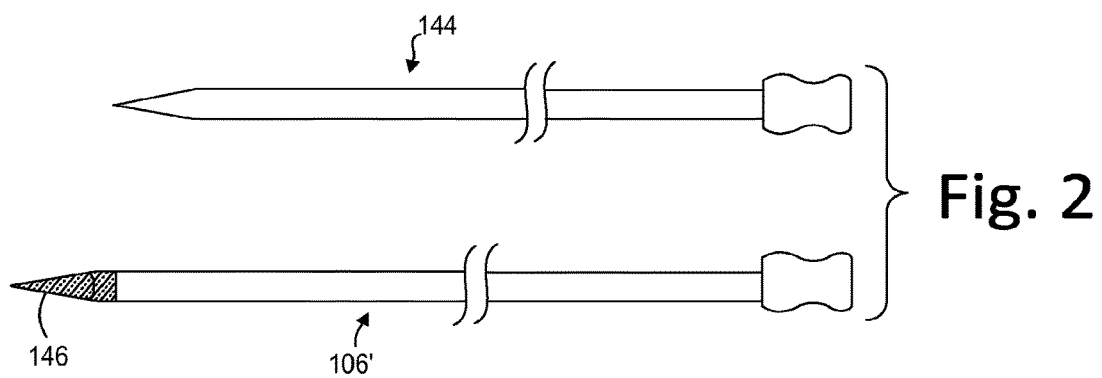
FIG. 2 is a plan view of alternative ablation probe and trocar that can be used in the kit of FIG. 1.

As illustrated in FIG. 2, an obturator, e.g., a conventional trocar 144, can be used to introduce the cannula 102 through the tissue, in which case, an alternative ablation probe 106' with a tapered open tissue-penetrating tip 146 can be used in place of the biopsy needle 104 to obtain a tissue sample via tissue coring. Even more alternatively, the use of a separate trocar allows the probe shaft 136 to be composed of a flexible material and/or the distal end 112 of the probe shaft 136 to be blunted.

Figure 4:
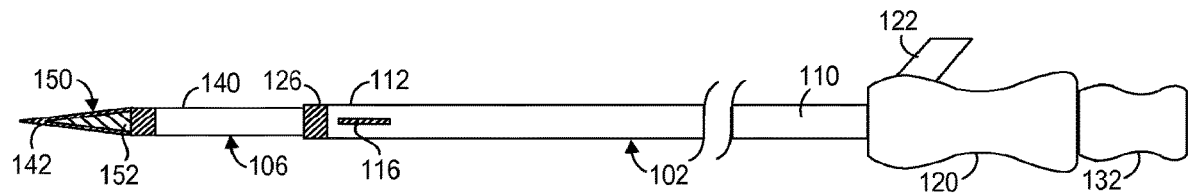
FIG. 4 is a side view of the combination of the delivery cannula and ablation probe used in the kit of FIG. 1.

Referring back to FIG. 1, the probe shaft 136, in the preferred embodiment, is composed of an electrically conductive material, such as stainless steel. In this case, the exterior surface of the probe shaft 136, with the exception of the distal tip 142, is preferably composed of an electrically insulative material 148. Alternatively, the probe shaft 136 may be composed of an electrically insulative material, such as a medical grade plastic, in which case, a separate insulative coating is not needed. As best shown in FIG. 4, the probe shaft 136 has a suitable length that is slightly longer than the length of the cannula shaft 108, so that the distal tip 142 of the probe shaft 136 extends from the distal end 112 of the cannula shaft 108 when the ablation probe 106 is completely introduced into the delivery lumen 114. The probe shaft 136 has an outer diameter that conforms with the inner diameter of the cannula 102. Preferably, the outer diameter of the probe shaft 136 and the inner diameter of the cannula shaft 108 are closely toleranced to prevent tissue-coring during the introduction of the cannula 102 and ablation probe 106.

Figure 5:
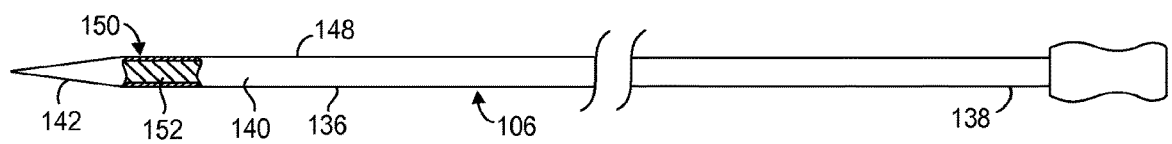
FIG. 5 is a side view of an alternative embodiment of an ablation probe that can be used in the kit of FIG. 1.

The ablation probe 106 further comprises an RF ablation electrode 150 carried by the distal end 140 of the probe shaft 136. In the preferred embodiment, the electrode 150 is formed by the exposed portion of the shaft distal tip 142. As illustrated, the electrode 150 encompasses the entire distal tip 142 and a cylindrical portion 152 just proximal to the distal tip 142. Alternatively, to increase the tissue-penetrating function of the ablation probe 106, the distal tip 142 can be composed of a relatively hard material, such as ceramic. In this case, the ablation electrode 150 is only formed by the cylindrical distal portion 152 of the probe shaft 136, as illustrated in FIG. 5. Alternatively, if the probe shaft 136 is composed of an electrically insulative material, the distal tip 142 can be coated with an electrically conductive material to form the electrode thereon, or a discrete ring electrode can be interference fit at the base of the distal tip 142. In this alternative case, a separate RF wire (not shown) will need to be routed from the electrode back through a lumen (not shown) with the probe shaft 136. Thus, as shown in FIG. 4, it can be appreciated that the RF electrodes 126 and 150 of the respective cannula 102 and ablation probe 106 can be located a distance from each other to establish a bipolar relationship. This distance can be varied simply by displacing the ablation probe 106 within the delivery lumen 114, thereby providing a means for modifying the size of the resulting ablation lesion.

Figure 6:
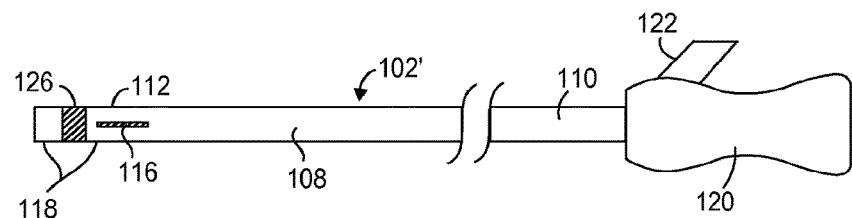
FIG. 6 is a side view of an alternative embodiment of a delivery cannula that can be used in the kit of FIG. 1.

It should be noted that the ablation electrodes 126 and 150 need not be located at the distal-most portions of the cannula shaft 108 and probe shaft 136. For example, FIG. 6 illustrates an alternatively embodiment of a cannula 102', wherein the distal-most portion of the cannula shaft 108 is coated with an insulative material, and a cylindrical portion just proximal to this insulated portion is exposed to form an ablation electrode 150.

Referring back to FIG. 1, the ablation probe 102 further comprises a handle 154 with an electrical connector 156 with which an RF cable (not shown) mates. The respective RF cables leading to the electrical connectors 122 and 156 of the cannula 102 and ablation probe 106 are connected to the positive and negative poles (or vice versa) of an RF generator (not shown), such that RF energy is delivered from the RF generator to the RF electrodes 126 and 150 on the respective cannula 102 and ablation probe 106 in a bipolar fashion.

The RF generator (not shown) may be a conventional RF power supply that operates at a frequency in the range from 200 KHz to 1.25 MHz, with a conventional sinusoidal or non-sinusoidal wave form. Such power supplies are available from many commercial suppliers, such as Valleylab, Aspen, and Bovie. Most general purpose electrosurgical power supplies, however, operate at higher voltages and powers than would normally be necessary or suitable for vessel occlusion. Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 20 W to 200 W, usually having a sine wave form, although other wave forms would also be acceptable. Power supplies capable of operating within these ranges are available from commercial vendors, such as Boston Scientific Corporation of San Jose, Calif., who markets these power supplies under the trademarks RF2000™ (100 W) and RF3000™ (200 W).

Figure 7:
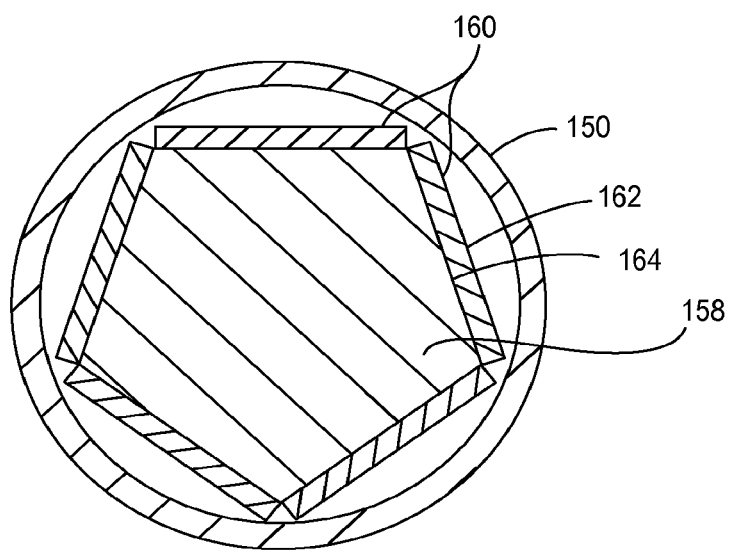
FIG. 7 is a cross-sectional view of the ablation probe illustrated in FIG. 1, taken along the line 7-7.

Referring still to FIG. 1, the ablation electrode 150 can be optionally cooled to provide for a more efficient tissue ablation and prevent tissue charring. To this end, the ablation probe 106 comprises a heat sink 156 composed of a thermally conductive material, such as aluminum. The heat sink 156 comprises a rod 158 that extends through the lumen 114 of the probe shaft 136 and out from the handle 154, and cooling fins (not shown) formed at the proximal end of the heat sink rod 158 and exposed to the ambient air. As shown in FIG. 7, the distal end of the heat sink rod 158 is disposed within the electrode 150.

The ablation probe 106 further comprises a number of thermoelectric devices 160 (in this case, five) circumferentially arranged and mounted to the external distal surface of the heat sink rod 158. Each thermoelectric device 160 comprises a cold side 162, which is in thermal communication with the cylindrical portion of the electrode 150, and a hot side 164, which is in thermal communication with the heat sink rod 158. When a DC signal with the proper polarity is applied to the thermoelectric devices 160 via wires (not shown), the cold and hot sides 162 and 164 of the thermoelectric devices 160 become cold and hot, respectively. As a result, thermal energy from the electrode 150 is absorbed by the cold sides 162 of the thermoelectric devices 160, which is then conducted to the hot sides 164 of the thermoelectric devices 160. The thermal energy emitted from the hot sides 164 of the thermoelectric devices 160 is then conducted through the heat sink rod 158 to the heat sink fins, where it dissipates into the ambient air. Further details on the structure and function of thermoelectric devices in ablation probes are disclosed in U.S. patent application Ser. No. 10/802,092, now U.S. Pat. No. 7,238,184, which is expressly incorporated herein by reference.

It should be noted that means other than using thermoelectric devices can be used to cool the ablation probe 106. For example, a cooling medium, such as saline, can be delivered through the delivery lumen 114 of the cannula 102 via the delivery port 124, or the cooling medium can be delivered through the ablation probe 106 in a closed-loop or open-loop manner. If done in an open-loop manner, the ablation probe 106 can have a tissue-coring tip from which the cooling medium will be perfused.

Having described the structure of the tissue ablation system 100, its operation in treating targeted tissue will now be described. The treatment region may be located anywhere in the body where hyperthermic exposure may be beneficial. Most commonly, the treatment region will comprise a solid tumor within an organ of the body, such as the liver, kidney, pancreas, breast, prostrate (not accessed via the urethra), and the like. The volume to be treated will depend on the size of the tumor or other lesion, typically having a total volume from 1 cm$^3$ to 150 cm$^3$, and often from 2 cm$^3$ to 35 cm$^3$. The peripheral dimensions of the treatment region may be regular, e.g., spherical or ellipsoidal, but will more usually be irregular. The treatment region may be identified using conventional imaging techniques capable of elucidating a target tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound of the tumor or other lesion being treated, either intraoperatively or externally.

Figure 8A:
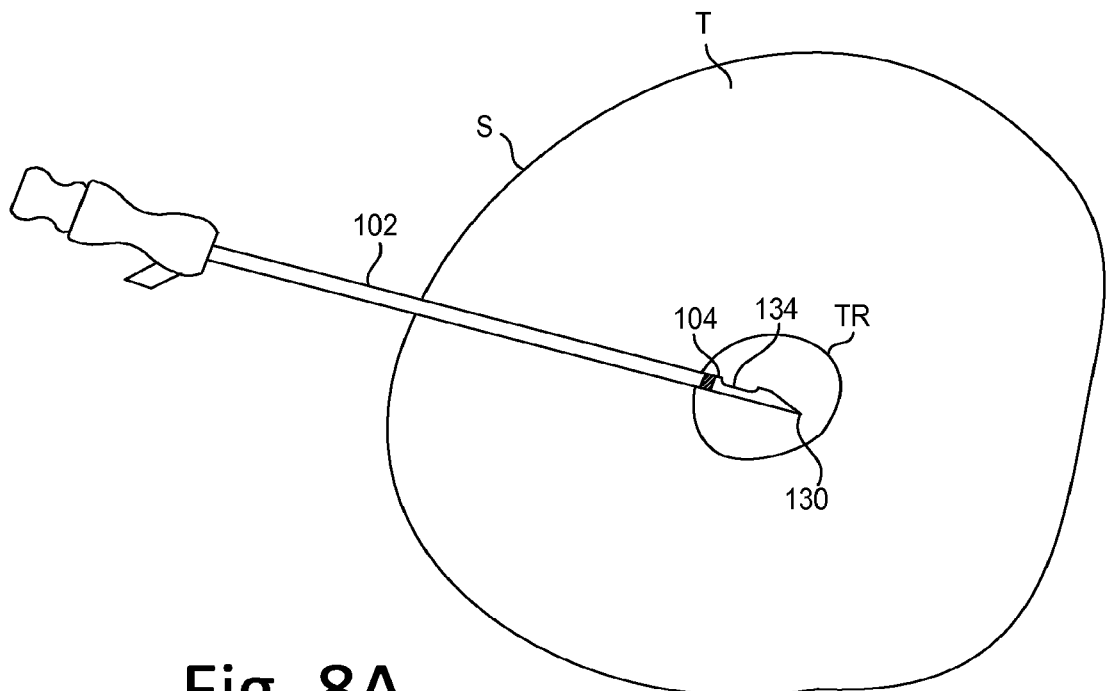
FIGS. 8A-8E illustrate cross-sectional views of one preferred method of using the tissue ablation kit of FIG. 1 to treat tissue.

Referring now to FIGS. 8A-8E, the operation of the tissue ablation kit 100 is described in treating a treatment region TR within tissue T located beneath the skin or an organ surface S of a patient. The delivery cannula 102 is first introduced through the tissue T, so that the distal end 112 of the delivery cannula 102 is located at the treatment region TR, as shown in FIG. 8A. This can be accomplished using any one of a variety of techniques. In the preferred method, the biopsy stylet 104 is introduced into the delivery lumen 114 of the cannula 102, and then the cannula 102 with the stylet 104, is introduced to the treatment region TR percutaneously directly through the patient's skin or through an open surgical incision. In this case, the sharpened tip 130 of the stylet 104 facilitates introduction to the treatment region TR. Alternatively, the ablation probe 106 or trocar 144 can be introduced into the delivery lumen 114 of the cannula 102, in which case, the cannula 102 with the ablation probe 106 or trocar 144, can be introduced to the treatment region TR. The sharpened distal tip 142 of the ablation probe or sharpened distal tip of the trocar 144 facilitates introduction to the treatment region TR in this case. Because the stylet 104, ablation probe 106 or trocar 144 are sufficiently rigid, i.e., have a sufficient column strength, the cannula 102 need not be rigid, but instead can be flexible if desired. In any event, delivery cannula 102 can be properly positioned relative to the treatment region TR under ultrasonic or other conventional imaging.

Figure 8B:
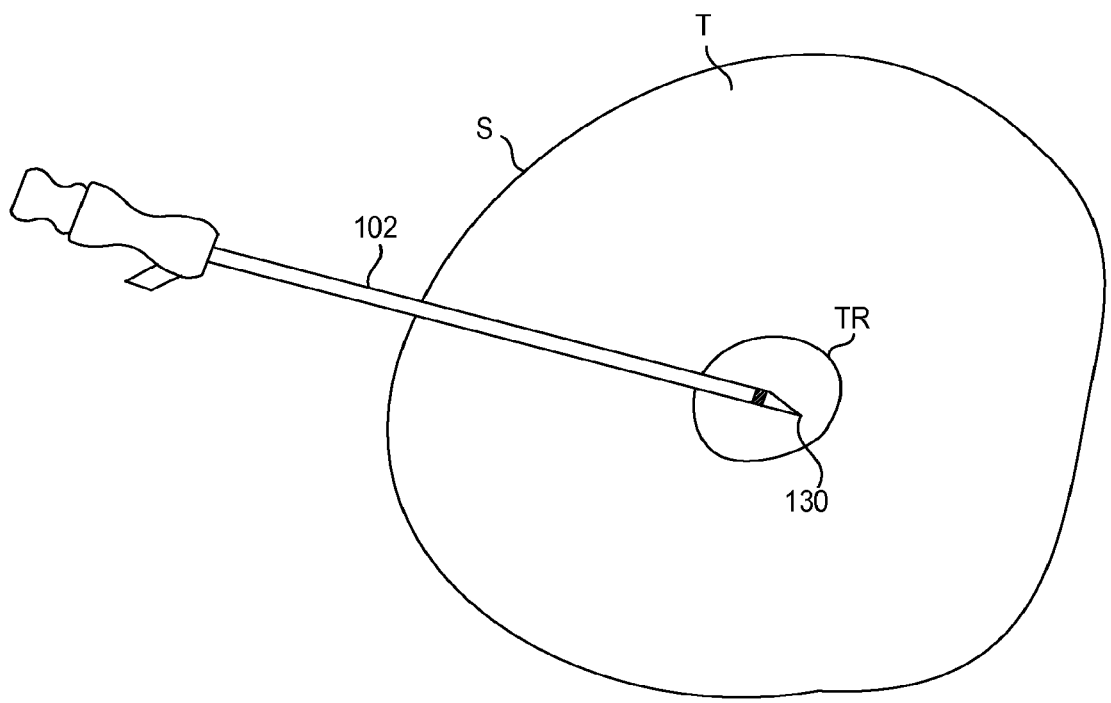

If the ablation probe 106 or trocar 144, instead of the stylet 104, is used to introduce the delivery cannula 102 to the treatment region TR, the stylet 104 can be exchanged for the ablation probe 106 or trocar 144. In particular, the ablation probe 104 or trocar 144 are removed from the delivery lumen 114, and then the stylet 104 can be introduced into the delivery lumen 114. After the delivery cannula 102 is properly placed with the distal tip 130 of the biopsy stylet 104 deployed, a sample of the treatment region TR is obtained by distally advancing the delivery cannula 102 over the stylet 104 in order to shear off tissue within the notch 134 (FIG. 8B). The stylet 104 is then removed from the delivery lumen 114 in order to retrieve the tissue sample for analysis in a laboratory. Of course this is just one exemplary method of taking a tissue sample, and other conventional biopsy devices can be introduced through the delivery lumen 114 of the cannula 102 in order to obtain a tissue sample.

Figure 8C:
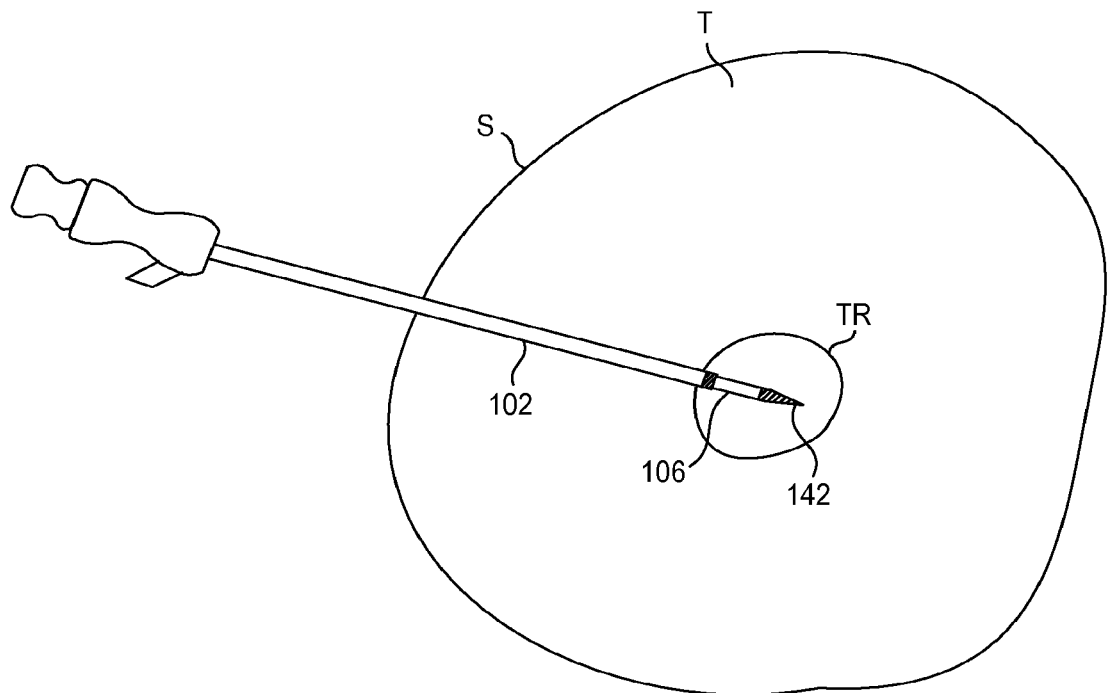
Figure 8D:
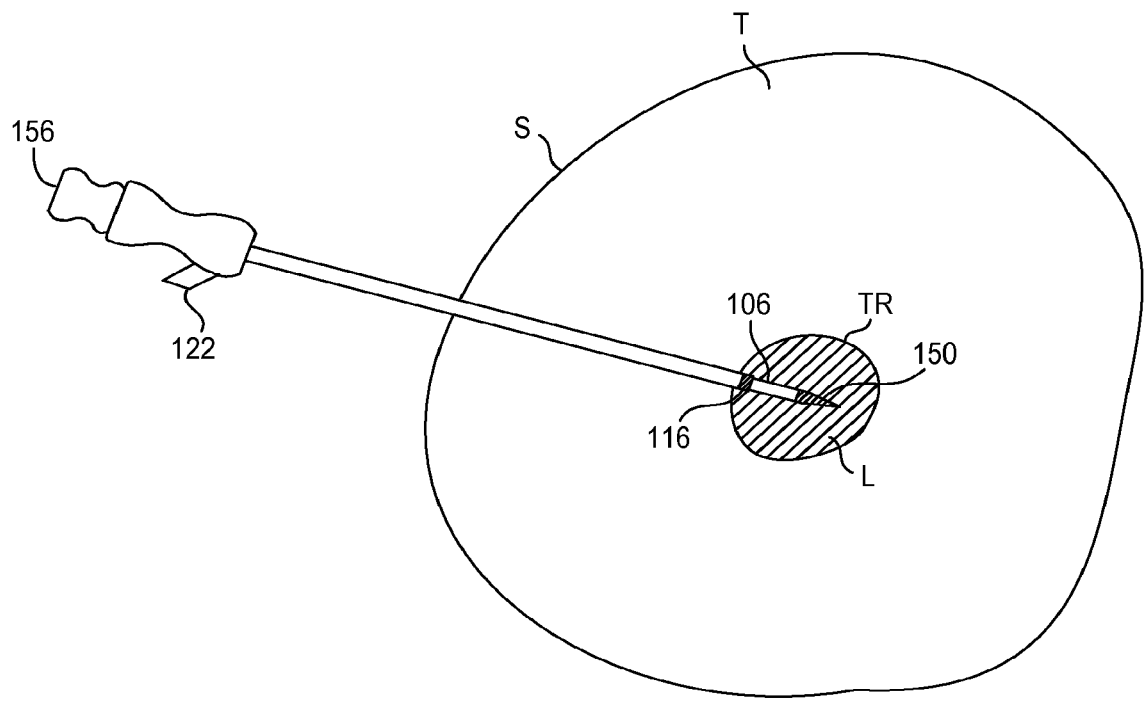

The ablation probe 104 is then introduced through the delivery lumen 114 until the distal tip 142 of the probe shaft 136 is placed into contact with the treatment region TR (FIG. 8C). The RF generator (not shown) is then connected to the electrical connectors 122 and 156 of the respective cannula 102 and ablation probe 106, thereby connecting the respective ablation electrodes 126 and 150 in a bipolar arrangement. The RF generator is then operated to ablate the treatment region TR. The thermoelectric devices 160 within the ablation probe 106 are preferably operated to cool the ablation electrode 150, thereby cooling the adjacent treatment region TR and providing for a more efficient ablation. As a result of the ablation process, a lesion L will be created, which will eventually expand to include the entire treatment region TR (FIG. 8D).

Preferably, prior to and/or during the ablation process, the distance between the ablation electrodes 126 and 150 are adjusted by moving the ablation probe 106 relative to the cannula 102. In this manner, the bipolar arrangement of the electrodes 126 and 150 can be customized to the particular treatment region TR. For example, if the treatment region TR is particularly large, the distance between the ablation electrodes 126 and 150 can be selected to be relatively great. In this manner, the number of times that the ablation probe 104 is moved may be minimized. On the other hand, if the treatment region TR is particularly small, the distance between the ablation electrodes 126 and 150 can be selected to be relatively small. In this manner, the risk of ablating healthy tissue and the ablation time is minimized. Alternatively, the treatment region TR can be iteratively ablated by gradually increasing the distance between the electrodes 126 and 150 (by moving the ablation electrode 150 deeper into the treatment region TR) between tissue ablations.

Figure 8E:
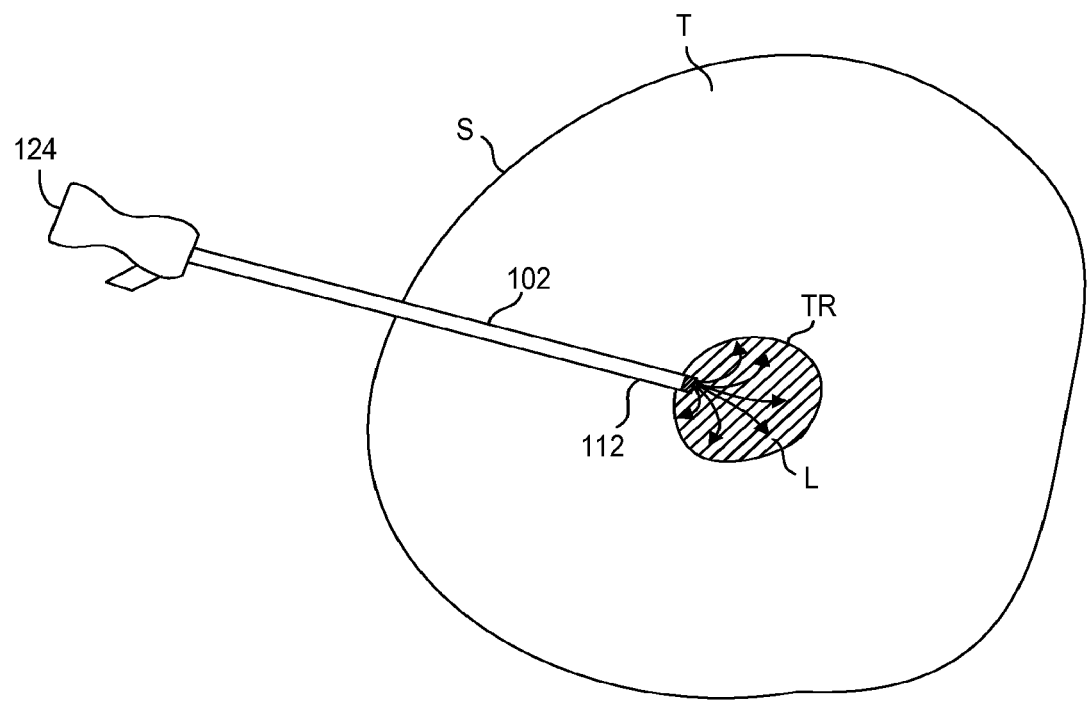

After the treatment region TR has been ablated, the ablation probe 106 is removed from the delivery lumen 114 of the cannula 102, and one or more chemotherapeutic agents are introduced into the delivery port 124, through the delivery lumen 114, and out the distal end 112 of the cannula 102, where it is perfused into the treatment region TR (FIG. 8E).

Useful chemotherapeutic agents can include, for example, paclitaxel, docetaxel, alkylating agents including mechlorethamine, chlorambucil, cyclophosphamide, melphalan and ifosfamide; antimetabolites including methotrexate, 6-mercaptopurine, 5-fluorouracil and cytarabine; plant alkaloids including vinblastine, vincristine and etoposide; antibiotics including doxorubicin, daunomycin, bleomycin, and mitomycin; nitrosureas including carmustine and lomustine; inorganic ions including cisplatin; biological response modifiers including interferon; enzymes including asparaginase; and hormones including tamoxifen and flutamide; their homologs, analogs, fragments, derivatives, pharmaceutical salts and mixtures thereof.

Thus, it can be appreciated that multiple medical elements, such as the biopsy stylet, ablation probe, and chemotherapeutic agents can be introduced through the delivery cannula using only one tissue path (i.e., the tissue path created by the initial introduction of the cannula 102 through the tissue), thereby substantially minimizing tissue trauma and imaging time.

Figure 9:
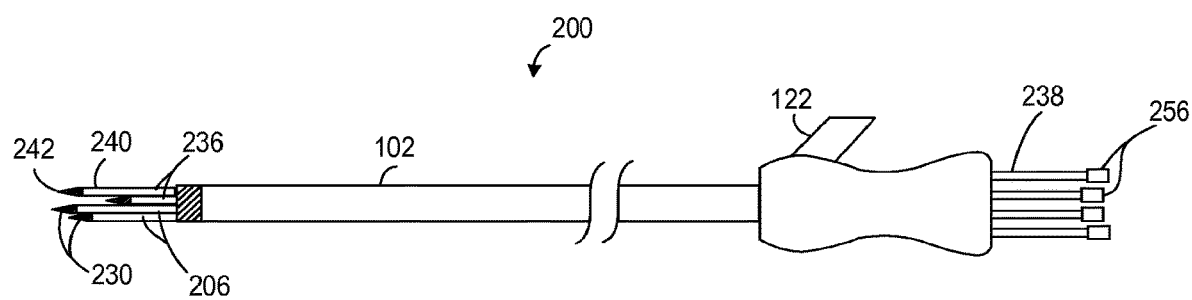
FIG. 9 is a plan view of another tissue treatment kit arranged in accordance with an alternative embodiment of the present invention.

Although the previously described embodiment was illustrated and described with only one ablation probe, it should be noted that multiple ablation probes can be used. For example, FIG. 9 illustrates another tissue treatment kit 200 arranged in accordance with a preferred embodiment of the present invention. The tissue treatment kit 200 generally comprises the previously described delivery cannula 102 and an array of ablation probes 206 configured to be independently introduced through the delivery cannula 102 in contact with the tissue to be treated. The tissue treatment kit 200 can optionally include the biopsy stylet 104 and/or trocar 144 previously described above.

Like the ablation probe 106, each of the ablation probe 206 comprises an elongated shaft 236 having a proximal end 238 and a distal end 240. The probe shaft 236 is preferably composed of a rigid or semi-rigid material, such that the probe shaft 236, but can be composed of a flexible material. The distal end 240 of the probe shaft 136 comprises a closed tissue-penetrating tip 242, which allows the cannula 102, in combination with the ablation probe 206 to be more easily introduced through tissue, while preventing tissue coring and minimizing tissue trauma. Preferably, a conventional trocar can be used to introduce the cannula 102 through the tissue.

Each ablation probe 206 further comprises an RF ablation electrode 250 carried by the distal end 212 of the respective probe shaft 236. Like the previously described electrode 150, the electrode 250 is formed by an exposed portion of the shaft distal tip 242. That is, each probe shaft 236 is composed of an electrically conductive material that is coated with an insulative material, with the exception of the distal tip 242. Each ablation probe 202 comprises an electrical connector 256 with which an RF cable (not shown) mates. Thus, the RF cable leading to the electrical connector 122 of the cannula 102 can be connected to the positive pole of an RF generator (not shown), and the respective RF cables leading to the electrical connectors 256 of the ablation probes 206 can be connected to the negative poles of the RF generator (or vice versa), such that RF energy is delivered from the RF generator to the RF electrodes 126 and 250 on the respective cannula 102 and ablation probes 206 in a bipolar fashion.

Use of the treatment kit 200 may be similar to that of the treatment kit 100, with the exception that multiple ablation probes 206, instead of a single ablation probe 106, will now be introduced through the delivery lumen 114 of the cannula 202.

Alternatively, a delivery cannula similar to the delivery cannula 202 can have a number of delivery lumens equal to the number of ablation probes 206. In this case, the ablation probes 206 can be introduced through the respective delivery lumens of the cannula 202. The delivery port 124 can be in fluid communication with any or all of the delivery lumens, and the biopsy stylet 104 can be selectively introduced through one of the delivery lumens.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of treating abnormal tissue within a patient, the method comprising:
   introducing a delivery cannula within the patient, the delivery cannula having a first electrode, a shaft, and a lumen extending through the shaft;
   introducing an ablation probe through the cannula lumen into contact with the abnormal tissue, the ablation probe having a second electrode;
   conveying ablation energy between the first electrode and the second electrode to ablate the abnormal tissue; and
   introducing a medical element through the cannula lumen into contact with the abnormal tissue, wherein the ablation probe is not present in the lumen when the medical element is introduced.

2. The method of claim 1, further comprising:
   introducing a biopsy stylet through the cannula lumen into contact with the abnormal tissue;
   removing a sample of the abnormal tissue with the biopsy stylet; and
   removing the biopsy stylet from the cannula lumen;
   wherein the ablation probe is introduced through the cannula lumen after removal of the biopsy stylet from the cannula lumen.

3. The method of claim 1, further comprising:
   introducing an obturator through the cannula lumen, wherein the delivery cannula is introduced into the patient while the obturator is in the cannula lumen; and
   removing the obturator from the cannula lumen;
   wherein the ablation probe is introduced through the cannula lumen after removal of the obturator from the cannula lumen.

4. The method of claim 1, further comprising, adjusting a distance between the first and second ablation electrodes by sliding the ablation probe relative to the delivery cannula.

5. The method of claim 1, further comprising cooling the abnormal tissue while conveying the ablation energy.

6. A method of treating abnormal tissue within a patient, the method comprising:
   positioning a delivery cannula within the patient, the delivery cannula having a shaft, a lumen extending through the shaft, a proximal end opening in communication with the lumen, a distal end opening in communication with the lumen, and a first ablation electrode disposed on a distal end of the shaft;
   introducing an ablation probe through the proximal end opening of the delivery cannula and the cannula lumen, and out the distal end opening of the delivery cannula, so that a second ablation electrode carried on the ablation probe contacts abnormal tissue within the patient;
   conveying ablation energy between the first and second ablation electrodes to ablate the abnormal tissue; and
   introducing a medical element through the proximal end opening of the delivery cannula and the cannula lumen, and out the distal end opening of the delivery cannula, into contact with the abnormal tissue, wherein the ablation probe is not present in the distal end opening of the delivery cannula when the medical element is introduced.

7. The method of claim 6, wherein the medical element is a medical instrument, the method further comprising removing the medical instrument from the cannula lumen prior to introducing the ablation probe through the cannula lumen.

8. The method of claim 6, wherein the medical element is a biopsy stylet.

9. The method of claim 6, wherein the medical element is a chemotherapeutic agent.

10. The method of claim 6, wherein the medical element is an obturator.

11. The method of claim 6, further comprising adjusting a distance between the first and second ablation electrodes by sliding the ablation probe relative to the delivery cannula.

12. The method of claim 6, further comprising coring the abnormal tissue with the ablation probe.

13. A medical probe kit comprising:
   a delivery cannula having
      a cannula shaft having a distal end and a proximal end,
      a cannula lumen extending through the cannula shaft, and
      a first ablation electrode disposed on the distal end of the cannula shaft;
   an ablation probe configured to be removably disposed within the cannula lumen via the proximal end of the cannula shaft, the ablation probe having
      a probe shaft having a distal end, and
      a second ablation electrode disposed on the distal end of the probe shaft, the second ablation electrode being arranged in a bipolar configuration with the first ablation electrode of the delivery cannula; and
   an elongated medical device configured to be removably disposed within the cannula lumen via the proximal end of the cannula shaft.

14. The medical probe kit of claim 13, wherein the ablation probe is slidable relative to the delivery cannula, whereby a distance between the first and second ablation electrodes can be adjusted.

15. The medical probe kit of claim 13, wherein the cannula shaft and the probe shaft are electrically conductive, and at least portions of the cannula shaft and probe shaft have an insulative coating, and the remaining portions of the cannula shaft and probe shaft form the first and second ablation electrodes.

16. The medical probe kit of claim 13, wherein the probe shaft has a distal tissue-penetrating tip.

17. The medical probe kit of claim 13, further comprising a biopsy stylet configured to be removably disposed within the cannula lumen.

18. The medical probe kit of claim 13, wherein the delivery cannula has a handle mounted to a proximal end of the cannula shaft, the handle comprising a fluid delivery port in fluid communication with the cannula lumen.

19. The medical probe kit of claim 13, further comprising an obturator configured to be removably disposed within the cannula lumen.

20. The medical probe kit of claim 13, further comprising a plurality of ablation probes configured to be removably disposed in the cannula lumen, wherein each of the ablation probes comprises a shaft and an ablation electrode disposed on a distal end of the shaft, and wherein the first ablation electrode is arranged in a bipolar configuration with the plurality of ablation electrodes.

* * * * *